(12) United States Patent
Vassallo et al.

(10) Patent No.: US 8,444,691 B2
(45) Date of Patent: May 21, 2013

(54) NASAL VALVE TREATMENT METHOD AND APPARATUS

(75) Inventors: Charles Vassallo, Oxford, CT (US); Susan L. Critzer, Dellwood, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/085,161

(22) Filed: Apr. 12, 2011

(65) Prior Publication Data

US 2011/0190884 A1    Aug. 4, 2011

Related U.S. Application Data

(62) Division of application No. 11/144,354, filed on Jun. 3, 2005, now Pat. No. 7,947,076.

(51) Int. Cl.
*A61F 2/18* (2006.01)
*A61B 17/34* (2006.01)

(52) U.S. Cl. .......................... 623/10; 606/185

(58) Field of Classification Search ............... 600/7–8; 606/116–117, 185, 199; 623/10, 14.12; 604/272
See application file for complete search history.

(56) References Cited

U.S. PATENT DOCUMENTS

| | | | |
|---|---|---|---|
| 261,501 A | 7/1882 | Vandermark | |
| 3,395,709 A | 8/1968 | Rubin | |
| 4,055,378 A | 10/1977 | Feneberg | |
| 4,105,035 A | 8/1978 | Rella | |
| 4,147,164 A | 4/1979 | Behney | |
| D263,747 S | 4/1982 | Jaramillo et al. | |
| 4,700,692 A * | 10/1987 | Baumgartner | 600/7 |
| 4,753,636 A | 6/1988 | Free | |
| 4,778,466 A | 10/1988 | Brotman | |
| 4,787,903 A | 11/1988 | Grendahl | |
| 4,898,461 A | 2/1990 | Portney | |
| 4,900,304 A * | 2/1990 | Fujioka et al. | 604/60 |
| 4,938,234 A | 7/1990 | Capriotti | |
| 4,941,874 A * | 7/1990 | Sandow et al. | 604/60 |
| 4,950,234 A * | 8/1990 | Fujioka et al. | 604/60 |
| 4,995,714 A | 2/1991 | Cohen | |
| 4,995,715 A | 2/1991 | Cohen | |
| 5,030,232 A | 7/1991 | Pham | |
| 5,076,684 A | 12/1991 | Simpson | |
| 5,084,057 A | 1/1992 | Green et al. | |
| 5,094,233 A | 3/1992 | Brennan | |
| 5,098,439 A * | 3/1992 | Hill et al. | 606/107 |

(Continued)

FOREIGN PATENT DOCUMENTS

| WO | WO 2005/082452 A1 | 9/2005 |
|---|---|---|
| WO | WO 2006/072571 A1 | 7/2006 |

OTHER PUBLICATIONS

Cole, P., "Biophysics of Nasal Airflow: A Review," *American Journal of Rhinology*, vol. 14, No. 4, pp. 245-249 (Jul.-Aug. 2000).

(Continued)

*Primary Examiner* — Andrew Iwamaye
(74) *Attorney, Agent, or Firm* — Merchant & Gould P.C.

(57) ABSTRACT

A method and apparatus for treating a nasal valve condition including surgically forming an access path to create a pocket on a side of the patient's nose. The pocket is positioned between a soft tissue layer and opposing surfaces of upper and lower cartilages of the nose. The pocket spans a junction between the upper and lower cartilages. An implant is placed through the access path into the pocket with a length oriented to span the junction. A delivery system for placement of the implant includes a surgical tool for forming the access path and for delivering the implant into the access path.

3 Claims, 8 Drawing Sheets

U.S. PATENT DOCUMENTS

| | | | |
|---|---|---|---|
| 5,112,353 | A | 5/1992 | Johansson et al. |
| 5,116,111 | A | 5/1992 | Simpson |
| 5,117,306 | A | 5/1992 | Cohen |
| 5,120,120 | A | 6/1992 | Cohen |
| 5,166,711 | A | 11/1992 | Portney |
| 5,178,636 | A | 1/1993 | Silberman |
| 5,229,797 | A | 7/1993 | Futhey |
| 5,336,163 | A | 8/1994 | DeMane et al. |
| 5,413,600 | A | 5/1995 | Mittelman |
| 5,533,499 | A | 7/1996 | Johnson |
| RE35,408 | E | 12/1996 | Petruson |
| 5,716,405 | A | 2/1998 | Mittelman |
| 5,782,913 | A | 7/1998 | Schindler et al. |
| 5,931,799 | A | 8/1999 | Guastella et al. |
| 5,984,890 | A * | 11/1999 | Gast et al. ............. 604/60 |
| 6,096,077 | A | 8/2000 | Callahan |
| 6,099,568 | A | 8/2000 | Simonian |
| 6,106,541 | A | 8/2000 | Hurbis |
| 6,110,207 | A | 8/2000 | Eichhorn |
| 6,186,965 | B1 | 2/2001 | Patterson |
| 6,203,560 | B1 | 3/2001 | Blach |
| 6,250,307 | B1 | 6/2001 | Conrad et al. |
| 6,261,243 | B1 * | 7/2001 | Burney et al. ............. 600/564 |
| 6,322,590 | B1 | 11/2001 | Sillers et al. |
| 6,347,241 | B2 * | 2/2002 | Burbank et al. ............. 600/431 |
| 6,357,436 | B1 | 3/2002 | Kreitzer et al. |
| 6,390,622 | B1 | 5/2002 | Muckenhirn |
| 6,431,174 | B1 | 8/2002 | Knudson et al. |
| 6,454,803 | B1 | 9/2002 | Romo, III |
| 6,595,998 | B2 * | 7/2003 | Johnson et al. ............. 606/90 |
| 6,626,172 | B1 | 9/2003 | Karow et al. |
| 6,632,245 | B2 | 10/2003 | Kim |
| 6,662,041 | B2 * | 12/2003 | Burbank et al. ............. 600/431 |
| 6,666,887 | B1 | 12/2003 | Callahan |
| 6,725,083 | B1 * | 4/2004 | Burbank et al. ............. 600/431 |
| 6,786,928 | B2 | 9/2004 | Callahan |
| 6,899,105 | B2 | 5/2005 | Krueger et al. |
| 6,921,415 | B2 | 7/2005 | Callahan |
| 6,993,375 | B2 * | 1/2006 | Burbank et al. ............. 600/431 |
| 6,996,433 | B2 * | 2/2006 | Burbank et al. ............. 600/431 |
| 7,001,341 | B2 * | 2/2006 | Gellman et al. ............. 600/562 |
| 7,047,063 | B2 * | 5/2006 | Burbank et al. ............. 600/431 |
| 7,060,723 | B2 * | 6/2006 | Ehring et al. ............. 514/438 |
| 7,093,938 | B2 | 8/2006 | Morris |
| 7,125,908 | B2 * | 10/2006 | Ehring et al. ............. 514/438 |
| 7,232,218 | B2 | 6/2007 | Morris |
| 7,416,533 | B2 * | 8/2008 | Gellman et al. ............. 600/562 |
| 7,651,505 | B2 * | 1/2010 | Lubock et al. ............. 606/116 |
| 7,670,350 | B2 * | 3/2010 | Selis ............. 606/151 |
| 7,780,734 | B2 * | 8/2010 | Johnson et al. ............. 623/17.16 |
| 7,811,331 | B2 * | 10/2010 | Johnson et al. ............. 623/17.16 |
| 7,905,885 | B2 * | 3/2011 | Johnson et al. ............. 606/90 |
| 7,947,076 | B2 | 5/2011 | Vassallo et al. |
| 2002/0000227 | A1 | 1/2002 | Duyke et al. |
| 2002/0004682 | A1 | 1/2002 | Zhou |
| 2002/0170564 | A1 | 11/2002 | Knudson et al. |
| 2002/0173848 | A1 | 11/2002 | Sachs |
| 2003/0033013 | A1 | 2/2003 | Callahan |
| 2003/0171812 | A1 * | 9/2003 | Grunberg et al. ............. 623/17.11 |
| 2003/0229614 | A1 | 12/2003 | Kotler |
| 2003/0233101 | A1 * | 12/2003 | Lubock et al. ............. 606/116 |
| 2004/0002746 | A1 | 1/2004 | Ryan et al. |
| 2004/0054374 | A1 * | 3/2004 | Weber et al. ............. 606/107 |
| 2004/0097980 | A1 | 5/2004 | Ferree |
| 2004/0097981 | A1 * | 5/2004 | Selis ............. 606/151 |
| 2005/0043706 | A1 * | 2/2005 | Eaton et al. ............. 604/500 |
| 2005/0049287 | A1 * | 3/2005 | Ehring et al. ............. 514/362 |
| 2005/0054695 | A1 * | 3/2005 | Ehring et al. ............. 514/362 |
| 2005/0055097 | A1 * | 3/2005 | Grunberg et al. ............. 623/17.11 |
| 2005/0101967 | A1 | 5/2005 | Weber et al. |
| 2005/0246016 | A1 | 11/2005 | Miller |
| 2006/0050234 | A1 | 3/2006 | Morris |
| 2006/0111646 | A1 * | 5/2006 | Gellman et al. ............. 600/562 |
| 2007/0066944 | A1 | 3/2007 | Nyte |
| 2009/0318875 | A1 | 12/2009 | Friedman |
| 2010/0145363 | A1 * | 6/2010 | Selis ............. 606/142 |
| 2011/0009971 | A1 * | 1/2011 | Johnson et al. ............. 623/17.16 |
| 2011/0098816 | A1 * | 4/2011 | Jacob et al. ............. 623/17.11 |
| 2011/0264228 | A1 * | 10/2011 | Johnson et al. ............. 623/17.16 |

OTHER PUBLICATIONS

Cole, P., "The Four Components of the Nasal Valve," *American Journal of Rhinology*, vol. 17, No. 2, pp. 107-110 (Mar.-Apr. 2003).

Ersek et al., "Minimally Invasive Macro Implants," *Worldplast*, vol. I, No. 4, pp. 275-285 (1996).

Fanous, N. et al., "Collapsed Nasal-Valve Widening by Composite Grafting to the Nasal Floor," *The Journal of Otolaryngology*, vol. 25, No. 5, pp. 313-316 (1996).

Huizing et al., "Functional Reconstructive Nasal Surgery," New York: Thieme. Screenshots were taken from Google Books website at http://books.google.com/books (2003).

Kalan, A. et al., "Treatment of External Nasal Valve (alar rim) Collapse with an Alar Strut," *The Journal of Laryngology & Otology*, vol. 115, pp. 788-791 (Oct. 2001).

Karen, M. et al., "The Use of Percutaneous Sutures for Graft Fixation in Rhinoplasty," *Arch Facial Plast. Surg.*, vol. 5, pp. 193-196 (Mar./Apr. 2003).

Mendelsohn, M., "Use of medpor splints to manage alar collapse," *Australian Journal of Oto-Laryngology*, downloaded from http://findarticles.com/p/articles/mi_qa3868/is_200101/ai_n8932300/ (2001).

Millman, B., "Alar Batten Grafting for Management of the Collapsed Nasal Valve," *The Laryngoscope*, vol. 112, pp. 574-579 (Mar. 2002).

Rhee, J. et al., "Nasal Valve Surgery Improves Disease-Specific Quality of Life," *The Laryngoscope*, vol. 115, pp. 437-440 (Mar. 2005).

Becker et al.; "Treatment of Nasal Obstruction from Nasal Valve Collapse with Alar Battent Grafts"—Begel House, Inc., copyright 2003; 11 pages.

Toriami et al.; "Rhinoplasty Dissection Manual"—Lippencott Williams & Wilkins, copyright 1999; 185 pages.

* cited by examiner

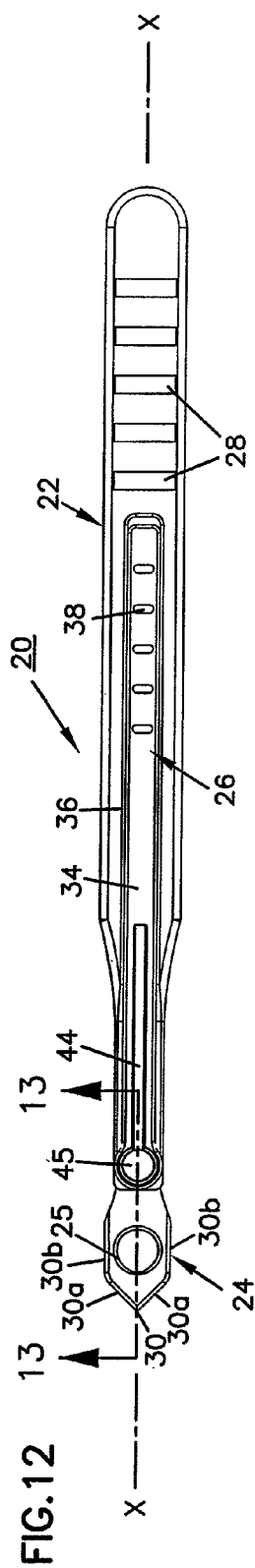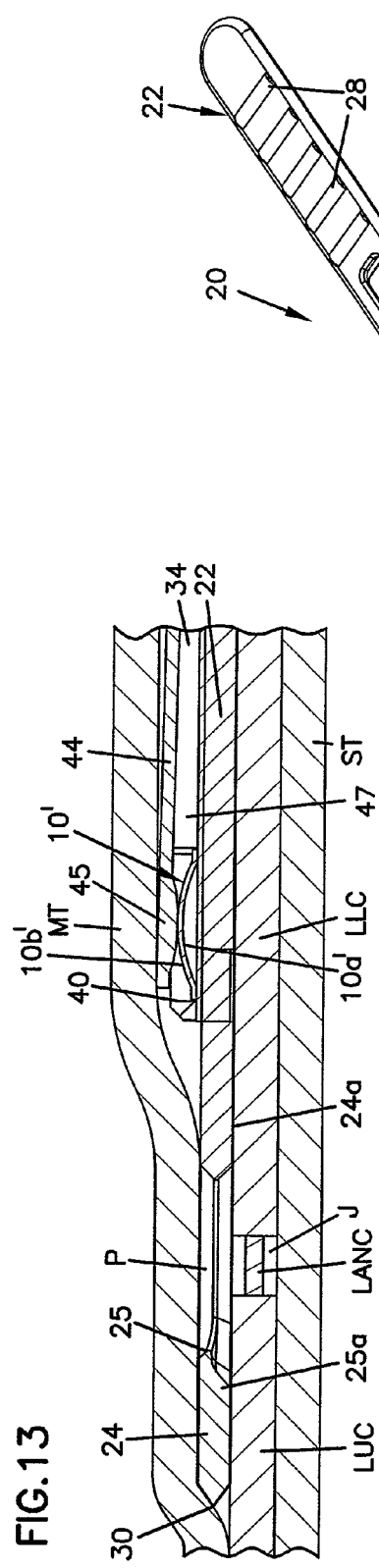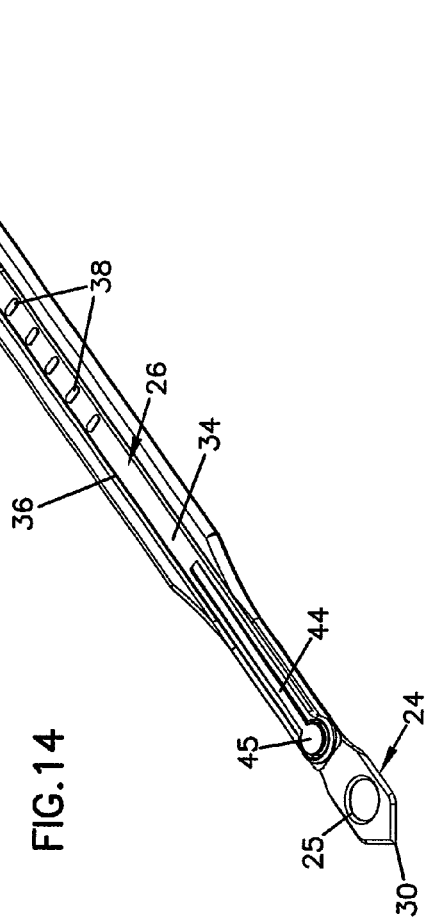
FIG.12
FIG.13
FIG.14

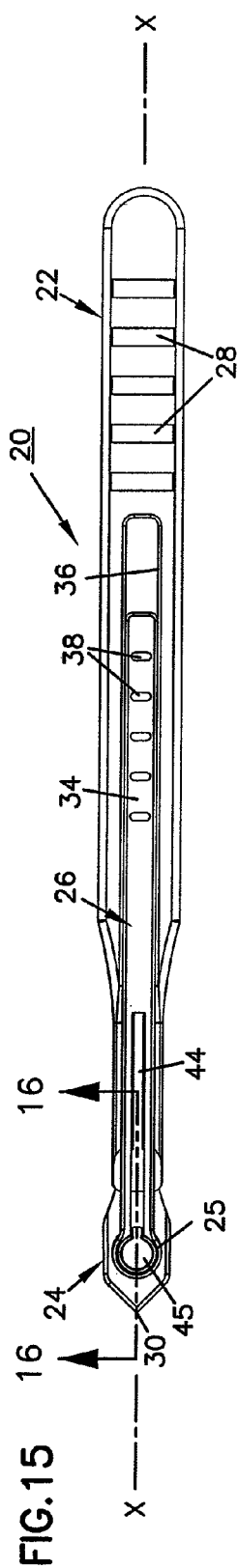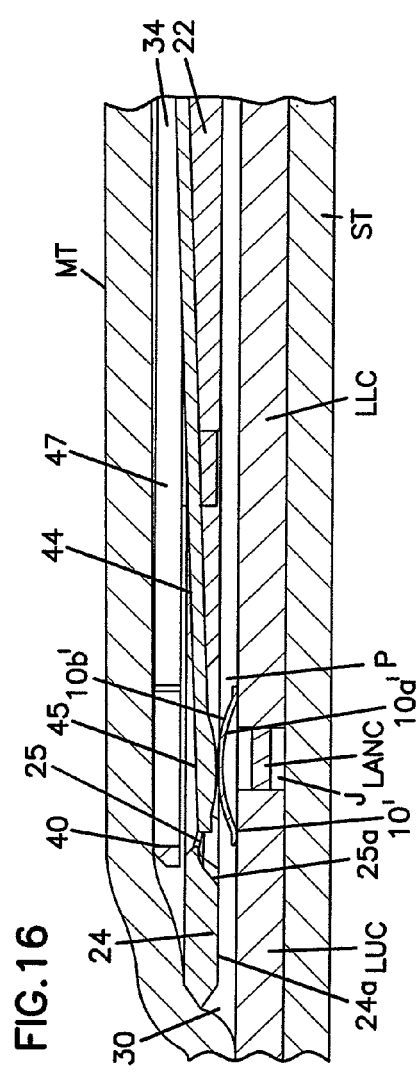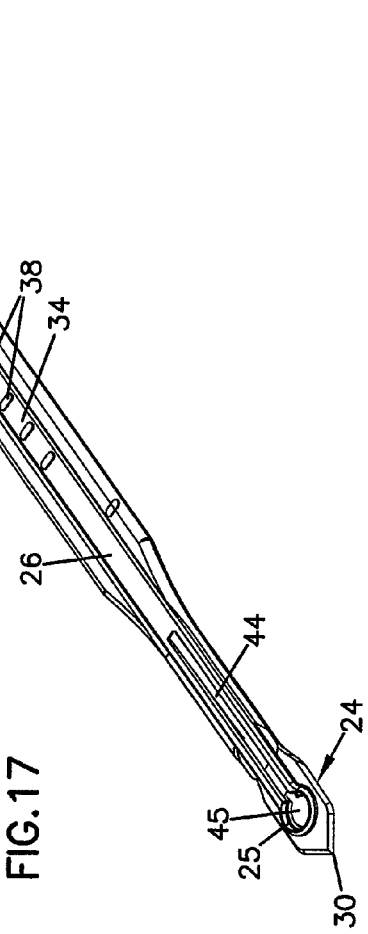
FIG.15
FIG.16
FIG.17

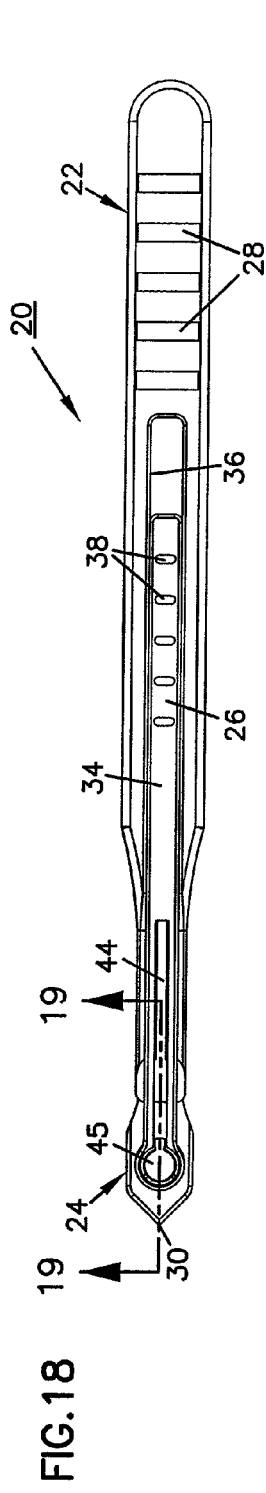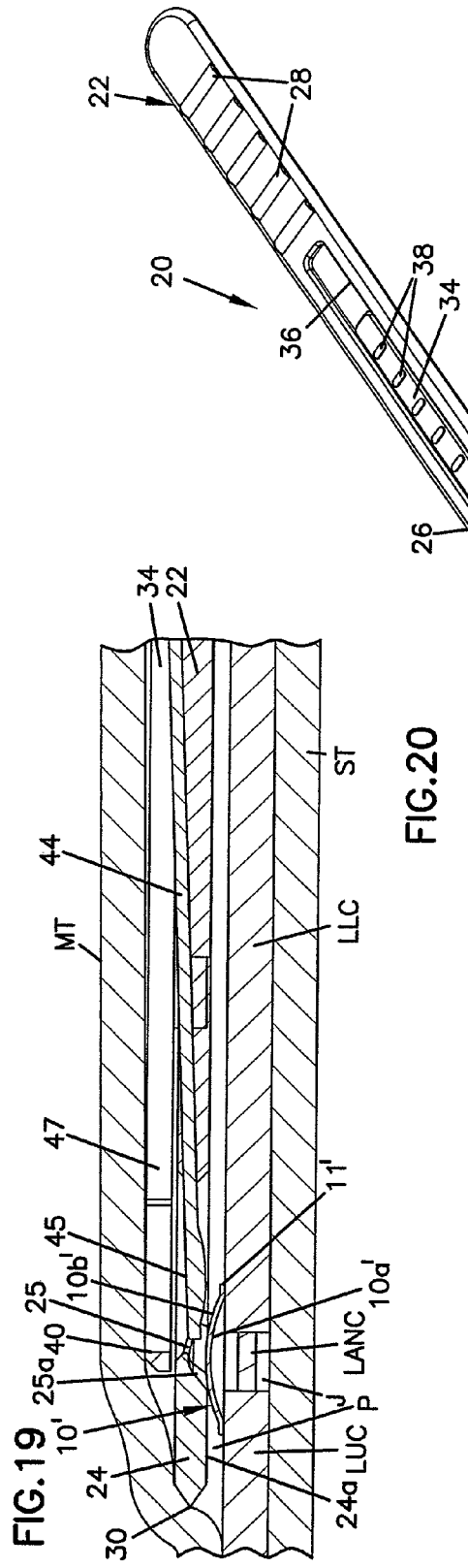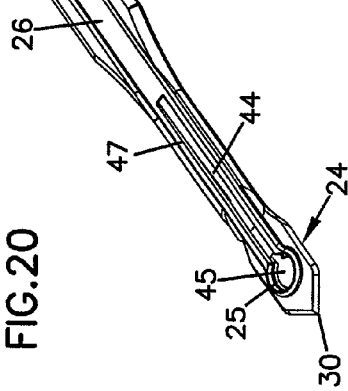
FIG.18
FIG.19
FIG.20

NASAL VALVE TREATMENT METHOD AND APPARATUS

I

CROSS REFERENCE TO RELATED APPLICATION

This application is a divisional of application Ser. No. 11/144,354, filed Jun. 3, 2005, now issued U.S. Pat. No. 7,947,076, which application is incorporated herein by reference in its entirety.

II

BACKGROUND OF THE INVENTION

1. Field of the Invention

This invention pertains to a treatment method and apparatus for treating a nasal valve. More particularly, this invention pertains to a method and apparatus for treating a nasal valve collapse.

2. Description of the Prior Art

Nasal valve dysfunction is a prevalent medical condition. Nasal valve collapse is due to weakness of the lateral wall of the nose. At the junction of the upper and lower nasal cartilages, this wall moves medially during the inspiratory phase of nasal breathing.

The nasal valve acts as a restriction to nasal airflow. The nasal valve disrupts the laminar flow characteristics of air, which would otherwise insulate the airflow from the mucosa of the nose. The nasal valve imparts an airflow disturbance which performs crucial nasal functions of mixing in the air stream and enhancing the air/mucosa contacts that are essential for effective exchanges of heat, water and contaminants between inspiratory air and the nasal mucosa. A description of the nasal valve and its functions are more fully described in Cole, "The Four Components of the Nasal Valve", *American Journal of Rhinology*, Vol. 17, No. 2, pp. 107-110 (2003). See also, Cole, "Biophysics of Nasal Air Flow: A Review", *American Journal of Rhinology*, Vol. 14, No. 4, pp. 245-249 (2000).

While the airflow restriction of the nasal valve is an important function, a weakened or otherwise compromised nasal valve can obstruct the nasal passage. Such compromise of the nasal valve can be a function of aging. Also, such compromise can result from prior nasal surgery which commonly include cosmetic surgeries.

Surgery to strengthen the nasal valve has been shown to significantly improve quality of life. Rhee, et al., "Nasal Valve Surgery Improves Disease—Specific Quality of Life", *Laryngoscope*, Vol. 115, pp. 437-440 (2005). The most common procedure for treating nasal valve collapse is so-called alar batten grafting. In batten grafting, a patient's cartilage is harvested from any one of a number of locations such as the nasal septum or the ear. The cartilage is sculpted to an appropriate size and shape and beveled on the edges for improved cosmetics. The batten graft is placed through either an external or endonasal approach. A pocket is formed overlying the cartilages of the nose with the pocket sized to receive the batten graft. Placement of the batten graft is shown in FIG. 4 (page 577) of Millman, et al., "Alar Batten Grafting for Management of the Collapsed Nasal Valve", *Laryngoscope*, Vol. 112, pp. 574-579 (2002). Other nasal valve surgeries are described in Kalan, et al., "Treatment of External Nasal Valve (Alar Rim) Collapse with an Alar Strut", *Journal of Laryngology and Otology*, Vol. 115, pages 788-791 (2001); Karen, et al., "The Use of Percutaneous Sutures for Graft Fixation in Rhinoplasty", *Archives Facial Plastic Surgery*, Vol. 5, pp. 193-196 (2003) and Fanous, "Collapsed Nasal-Valve Widening by Composite Grafting to the Nasal Floor", *Journal of Otolaryngology*, Vol. 25, No. 5, pp. 313-316 (1996).

The harvesting of a portion of the patient's natural cartilage is an additional procedure and requires sculpting or other modification of the graft prior to use. Accordingly, synthetic nasal dilators have been suggested. An example of such is found in U.S. Pat. No. 6,106,541 to Hurbis dated Aug. 22, 2000. In the '541 patent, the nasal dilator has a V-shape with an apex placed over the bridge of the nose to support the nose in a manner similar to that of external nasal dilators such as devices sold under the "BREATHE RIGHT" trademark by CNS Inc., 1250 Park Road, Chanhassen, Minn. 55317 and as shown in U.S. Pat. No. 5,533,499. Other types of external nasal dilators are known such as those described in U.S. Pat. No. RE. 35,408. Other examples include U.S. Pat. No. 6,322,590 to Sillers et al., dated Nov. 27, 2001. Less invasive procedures include the placement of a device within the nasal cavity without surgically implanting the device. However, such devices can be uncomfortable and may require the patient to remove and replace the device on a periodic basis.

The structure of an implant for treating the nasal valve should consider the ease by which such a device may be placed as well as cosmetic effects following placement of the device. Devices requiring a general anesthetic or intravenous anesthetic can only be placed in a hospital setting. It is desirable that a device for treating nasal valves be designed to accommodate placement in an office setting requiring only needle injection local anesthetic.

III

SUMMARY OF THE INVENTION

According to a preferred embodiment of the present invention, the method and apparatus are disclosed for treating a nasal valve condition. The method includes surgically forming an access path to create a pocket on a side of the patient's nose. The pocket is positioned between a soft tissue layer (external skin or nasal mucosa) and opposing surfaces of upper and lower cartilages of the nose. The pocket spans a junction between the upper and lower cartilages. An implant is selected having a length, width and thickness sized to reside within the pocket. The length is sized to span the junction. The width is sized to be less than the width of the upper and lower cartilages. The thickness of the implant is as thin as possible while maintaining material strength to resist bending in response to inhalation pressures at the nasal valve. The implant is placed through the access path into the pocket with the length oriented spanning the junction. A delivery system for placement of the implant includes a surgical tool for forming the access path and for delivering the implant into the access path.

IV

BRIEF DESCRIPTION OF THE DRAWINGS

FIG. 12 is a top plan view of a delivery apparatus according to the present invention shown in a fully retracted state;

FIG. 13 is a side sectional view taken along line 13-13 of FIG. 12 and showing the apparatus forming a pocket between nasal cartilage and mucosa and prior to delivery of the implant of FIGS. 10 and 11;

FIG. 14 is a top, front and left side perspective view of the delivery apparatus of FIG. 12;

FIG. 15 is the view of FIG. 12 showing the apparatus in position for delivery of the implant into a pocket formed between the cartilage and the mucosa;

FIG. 16 is a view similar to FIG. 13 and taken along line 16-16 of FIG. 15 showing the implant releasing from the delivery apparatus;

FIG. 17 is a perspective view of the apparatus of FIG. 15;

FIG. 18 is a view similar to that of FIGS. 12 and 15 showing a slider mechanism partially retracted for leaving an implant within a pocket;

FIG. 19 is a view similar to FIGS. 13 and 16 and taken along line 19-19 of FIG. 18 showing an implant within a formed pocket and showing partial retraction of a slider mechanism;

FIG. 20 is a perspective view of the apparatus of FIG. 18;

V

DESCRIPTION OF THE PREFERRED EMBODIMENT

With reference now the various drawing figures in which identical elements are numbered identically throughout, a description of the preferred embodiment of the present invention will now be provided.

A. Anatomy

Figure 1:
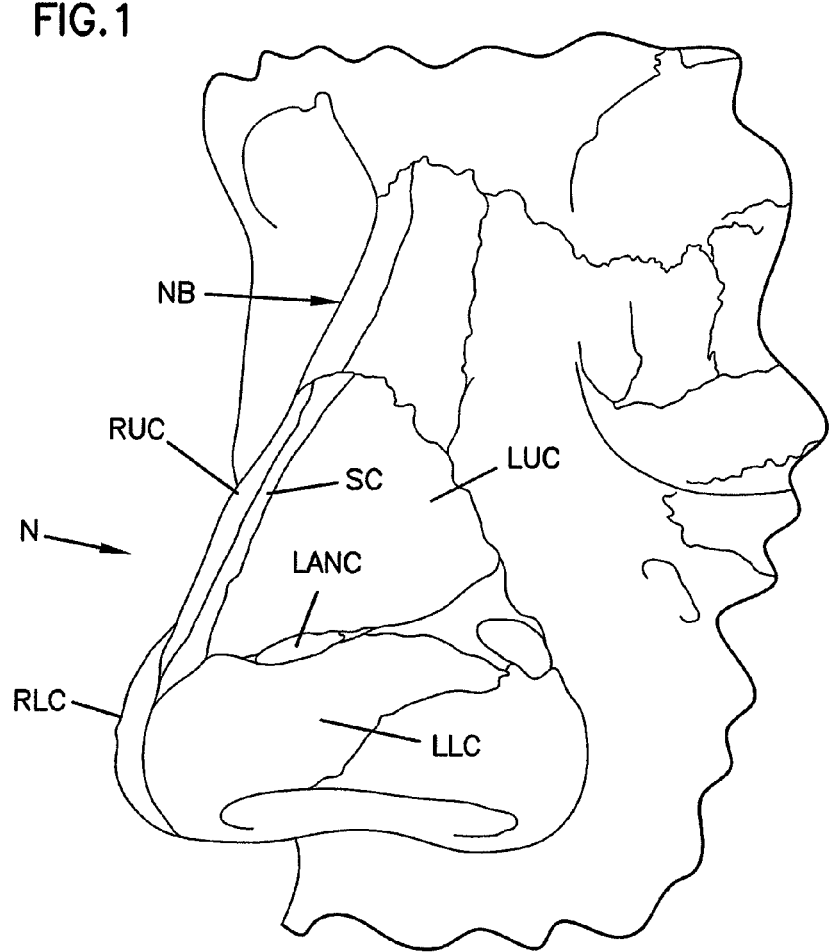
FIG. 1 is a perspective view of the front, top and left side of a patient's nose showing skeletal components and cartilages.
Figure 2:
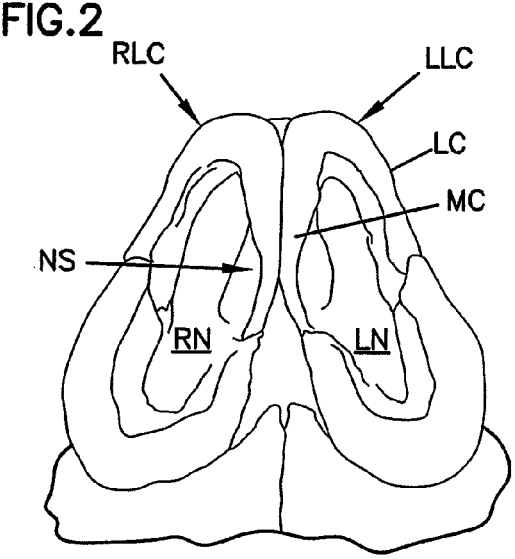
FIG. 2 is a bottom plan view of the components of FIG. 1.
Figure 3:
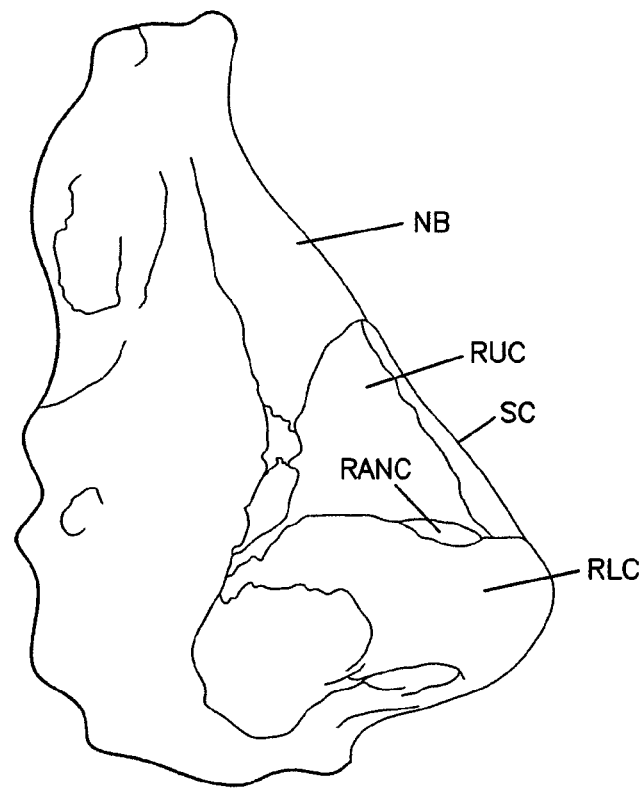
FIG. 3 is a right side elevation view of the components of FIG. 1.

Before proceeding with a description of the apparatus and method of the present invention, a review of relevant anatomy will facilitate an understanding of the present invention. FIGS. 1-3 show in perspective, bottom plan and right side elevation, respectively, components of the nose with skeletal muscle, soft tissue (such as external skin or nasal mucosa) and blood vessels removed.

The nose N includes nasal bone NB at an upper end of the nose. The bottom of the nose N includes the lower cartilage also referred to as the major alar cartilage. There is both a right lower cartilage RLC and a left lower cartilage LLC, which are generally symmetrical in structure.

The lower cartilages RLC, LLC include an external component referred to as the lateral crus LC and an internal component referred to as the medial crus MC. The medial crus and septal nasal cartilage create a nasal septum NS that divides the nose N into a left nostril LN and a right nostril RN.

Upper cartilages reside between the lower cartilages and the nasal bones NB. The upper cartilages include both a right upper cartilage RUC and a left upper cartilage LUC separated by a septal cartilage SC extending down the bridge of the nose N. The opposing edges of the lower cartilage LLC, RLC and upper cartilage LUC, RUC may move relative to one another. Disposed between the opposing edges is an accessory nasal cartilage (left and right) LANC, RANC.

Figure 4:
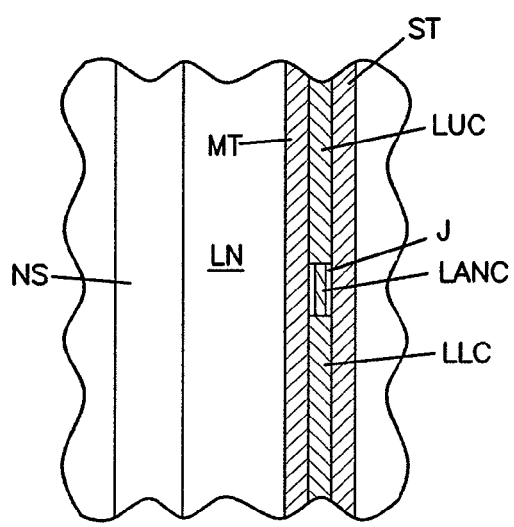
FIG. 4 is a schematic view of upper and lower cartilages (between inner and outer soft tissue layers) with the nasal valve components shown in a non-collapsed state.
Figure 5:
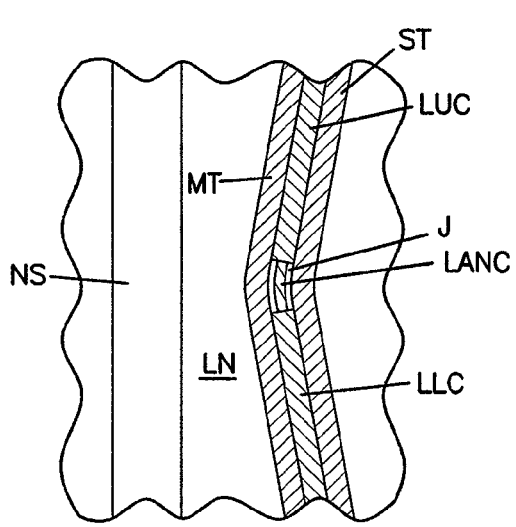
FIG. 5 is the view of FIG. 4 showing the nasal valve components shown in a collapsed state.

Both inner and outer surfaces of the cartilages LLC, RLC, LUC, RUC and LANC, RANC are covered with soft tissue shown schematically in FIGS. 4 and 5 as an inner mucosal tissue MT and an outer skin tissue ST. In FIGS. 4 and 5 only the left upper and lower cartilages LUC, LLC are shown with positioning relative to the septum NS.

When congested, during inhalation, airflow through the nostrils creates an inward pressure at the junction between the upper and lower cartilages. This pressure is expressed as a function of nasal resistance which is estimated as 10 centimeters of water per one liter per second. Cole, "The Four Components of the Nasal Valve", *American Journal of Rhinology*, pages 107-110 (2003).

In response to these forces, a weakened nasal valve may collapse inwardly as illustrated in FIG. 5. In FIG. 5, it will be appreciated that the inward deflection is exaggerated for ease of illustration. It will be noted with reference to FIGS. 4 and 5 that the junction between the upper and lower cartilages is a hinge point at the inward deflection.

B. Implant

Figure 8:
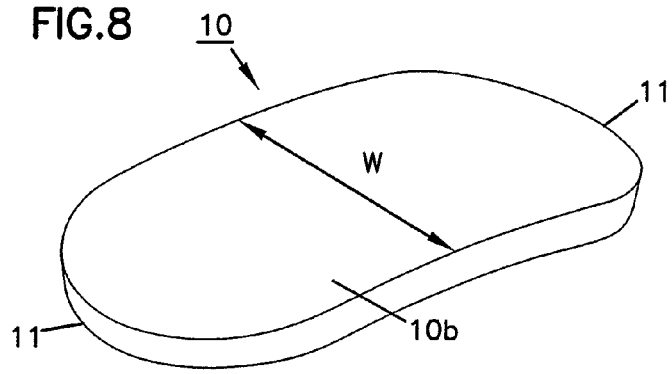
FIG. 8 is a perspective view of a first embodiment of an implant according to the present invention.
Figure 9:
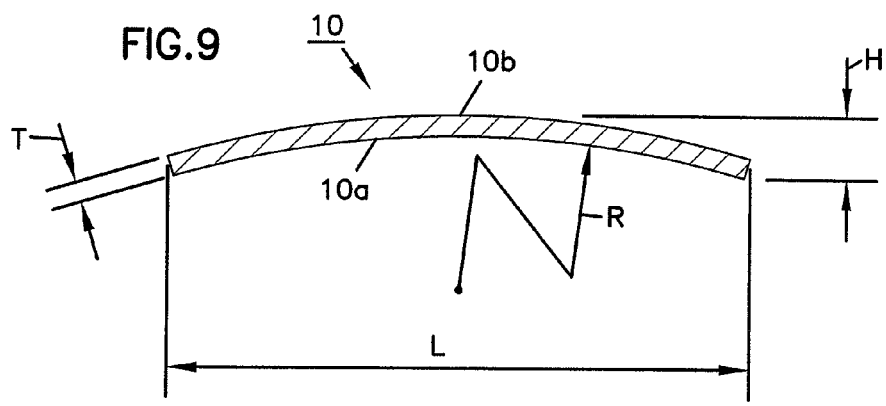
FIG. 9 is a side elevation view of the implant of FIG. 8.

FIGS. 8-11 illustrate examples of implants in which can be placed on the nasal cartilages for treatment according to the present invention. The implant of FIGS. 8 and 9 is substantially rectangular with the implant 10 having dimensions including a length L, width W and thickness T. The implant 10 has rounded ends 11. The flat implant 10 has a small curvature R between the ends 11 with the first surface 10a concave and the second surface 10b convex. The length L is sized to span the junction J (FIG. 6) between the upper and lower cartilages (i.e., greater than a spacing between LUC, LLC and RUC, RLC). The width W is sized to be less than the width W* (FIG. 6) of the upper and lower cartilages such that the apparatus 10 may be placed opposing the cartilages and reside completely on one side of the nose without extending over the bridge of the nose N. The width W of the implant 10 may be greater than the length L of the implant 10.

As will be more fully described, the implant 10 may be placed opposing the outer surfaces of the cartilages (between the cartilages and skin) or may be placed opposing the inner surfaces of the cartilages (between the cartilages and mucosa). The thickness T of the implant is selected so that when opposing the outer surfaces of the cartilages beneath a skin layer, the implant 10 does not substantially alter the external appearance of the skin. When placed opposing the internal surfaces of the cartilages, the implant thickness avoids adding to an obstruction or a narrowing of the nasal passage.

By way of a non-limiting example, the length L may be six millimeters, the width W three millimeters, and the thickness T may be 0.4 millimeters. The radius of curvature R is 12.5 mm. The height H is 0.74 mm. The height H is the distance between the plane of the ends 11 to the maximum thickness of the implant 10. In the event, the implant 10 is not formed with a curvature R, the height H equals the thickness T.

Figure 10:
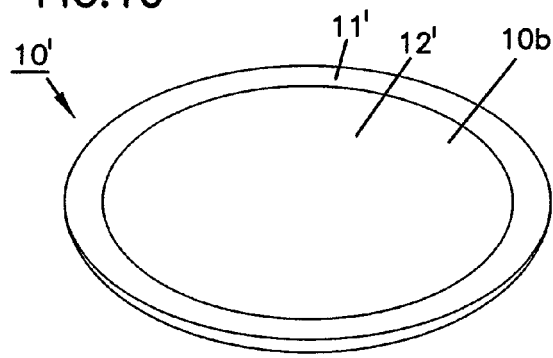
FIG. 10 is a perspective view of a second embodiment of the implant according to the present invention.
Figure 11:
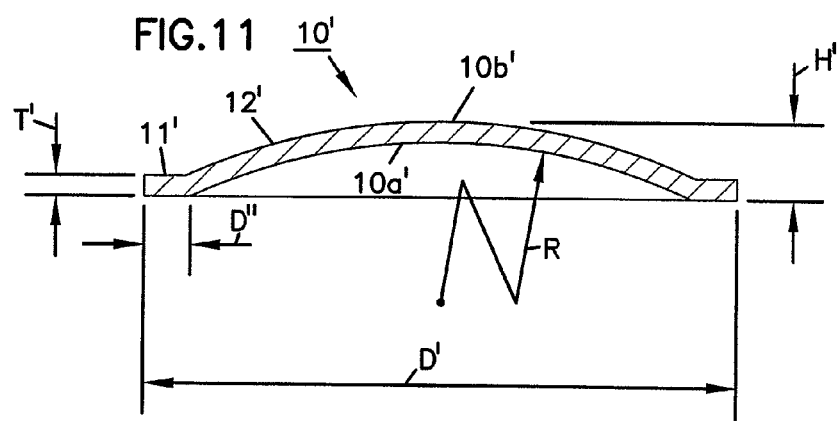
FIG. 11 is a side cross-sectional view of the implant of FIG. 10.

FIGS. 10 and 11 illustrate an alternative embodiment of the implant. The implant 10' is a disk having a diameter D' of 6 millimeters. For the purpose of interpreting the present application and the claims which are appended hereto, the disk 10' has a length of 6 millimeters and a width of 6 millimeters.

The disk 10' is a hollow dome 12' with a radius of curvature R' of 6.0 mm for a total height H' of 0.7 millimeters. The first surface 10a' of the implant 10' is concave and the second surface 10b' is convex. The disk 10' includes an annular flange portion 11' having a diameter D" of 0.5 millimeters. The wall thickness T' is 0.4 mm.

The disk 10' has an added advantage over the elongated implant 10 in that orientation of the implant 10' relative to the cartilage is not critical. Further, the dome 12 provides an opportunity for improved tactile feel for a surgeon identifying positioning of the implant 10' by feeling for the implant by palpating the soft tissue.

Figure 6:
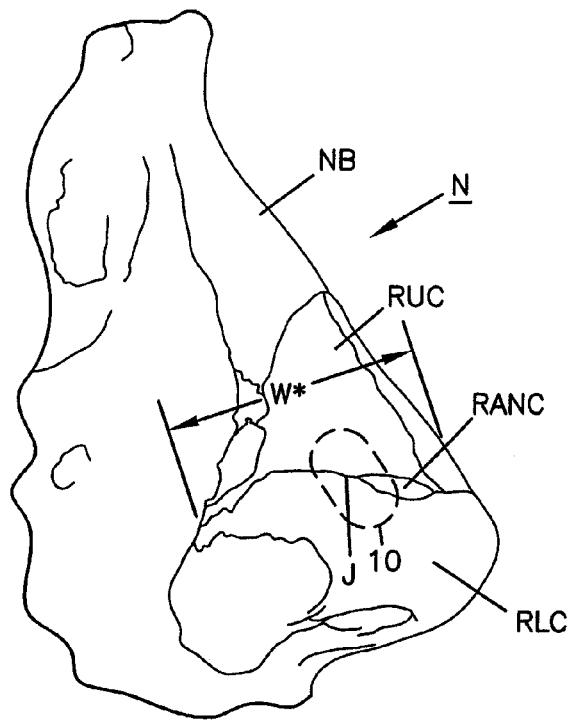
FIG. 6 is the view of FIG. 3 showing a relative placement of a first embodiment of an implant according to the present invention.
Figure 7:
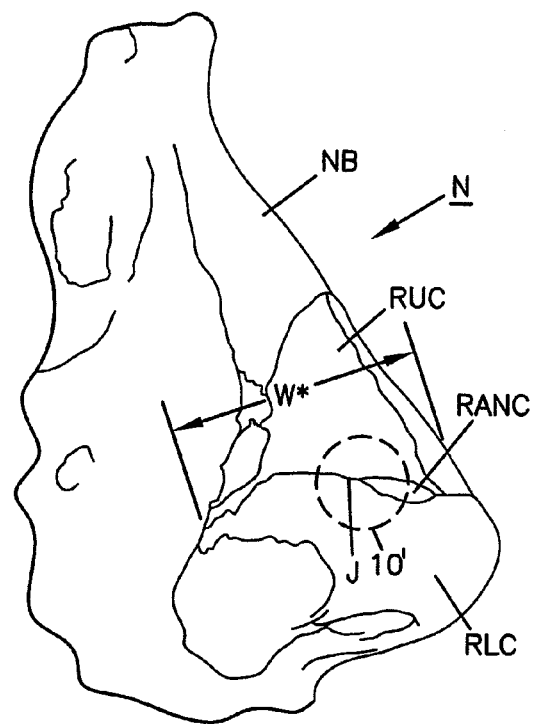
FIG. 7 is the view of FIG. 6 showing a relative placement of a second embodiment of an implant according to the present invention.

FIG. 6 shows placement of the implant 10 on the upper and lower cartilages RUC, RLC with the implant 10 spanning the junction J between the cartilages and residing completely on the right side of the nose. It will be appreciated that an identical implant identically placed is positioned on the left side of the nose overlying the left upper cartilage LUC and the left lower cartilage LLC. FIG. 7 is a similar view to that of FIG. 6 with the implant 10' similarly positioned spanning the upper and lower cartilages RUC, RLC.

Figure 21:
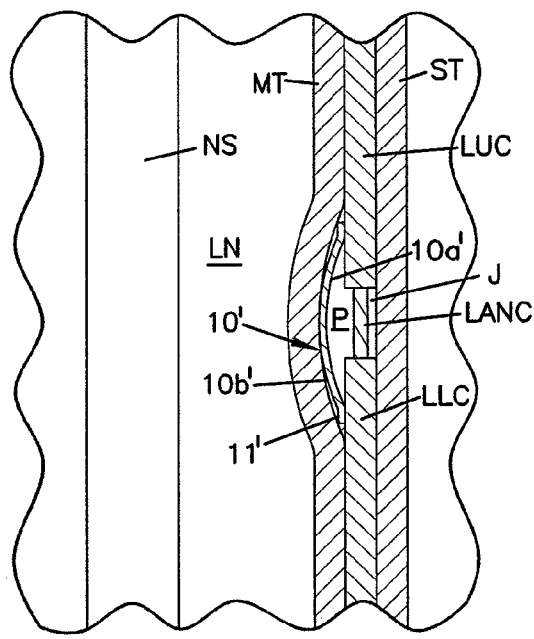
FIG. 21 is a view showing the implant of FIGS. 10 and 11 in a pocket between cartilage and mucosa and with the delivery tool fully retracted.
Figure 22:
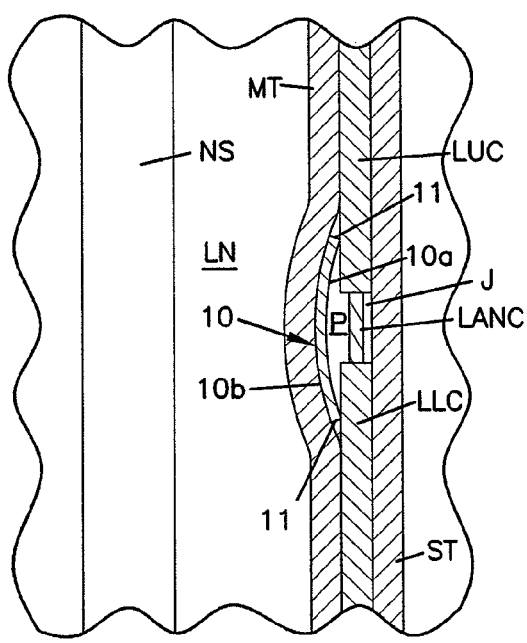
FIG. 22 is a view showing the implant of FIGS. 8 and 9 in a pocket between cartilage and mucosa and with the delivery tool fully retracted.

It will be appreciated that while the implants 10, 10' in FIGS. 6 and 7 are shown on the interior surfaces of the upper and lower cartilages RUC, RLC, the implants 10, 10' can be placed opposing the exterior surfaces of the upper and lower cartilages RUC, RLC with the same relative positioning over the junction J between the cartilages. FIGS. 21 and 22 show the implants 10', 10 placed against the internal surfaces of the cartilages LUC, LLC in a schematic representation with the implants 10', 10 spanning the junction J between the cartilages LUC, LLC. FIGS. 21 and 22 are not to scale and the amount of alteration of the contour of the mucosal tissue MT is exaggerated.

The implants 10, 10' may be formed of any suitable material such as steel, titanium, PTFE, hydroxyl apitite or any other bio-compatible material having a sufficient stiffness to resist deformation in response to the pressures and suctions within the nostril. While the implants 10, 10' are shown smooth, they could be provided with ribs or other raised surfaces or surface deformations to assist the surgeon in palpating for the implant following placement. Further, the devices 10, 10' could be provided with tissue in-growth surfaces either through surface modification or application of in-growth agents. Also, the devices could be drug-eluding to facilitate a healing process following implantation.

C. Delivery System

FIGS. 12-20 illustrate a delivery apparatus 20 for placing the implant in a minimally invasive procedure. Apparatus 20 includes a handle 22, a flat blade 24, and a slider mechanism 26. The apparatus 20 is preferably disposable with the handle 22 formed of rigid plastic and, at its proximal end, may include raised ribs 28 or other surface contours to facilitate gripping by a surgeon.

The blade 24 is secured to the handle 22 and projects away there from in a common plane. The blade 24 includes a blade tip 30 aligned with the longitudinal axis of the handle 22. Knife edges 30a extend outwardly and rearward away from the tip 30 on both sides thereof and include edges 30b extending substantially parallel and spaced from the longitudinal axis X-X of the handle 22.

The blade 24 includes an opening 25 extending through the blade 24. The opening 25 is sized to pass an implant as previously described. In the embodiment shown in the figures, the apparatus 20 is designed for delivery of the disk implant 10' of FIGS. 10 and 11. Accordingly, the opening 25 is circular in shape having a diameter greater than the diameter of the implant 10'. For delivery of the implant 10 of FIGS. 8 and 9, the opening 22 would be provided with a length aligned with the longitudinal axis of the handle 22 and with a length and width of the opening being greater than the length and width of the implant 10.

The slider mechanism 26 includes a body portion 34, which is received within a slot 36 formed in the handle 22. Accordingly, the sliding mechanism 26 may be urged by a surgeon to move along the longitudinal axis of the handle 22. The body portion 34 has raised ribs 38 for easy gripping by a surgeon.

A distal end of the slider 26 includes a hole 40 (FIG. 13) sized to receive the implant 10' and retain the implant in the hole 40 as the slider mechanism 26 is moved relative to the handle 22. The first surface 10a' of the implant 10' opposes the handle 22. In FIGS. 12-14, the slider mechanism 26 is shown in a retracted position with the hole 40 positioned proximal relative to the hole 25 and the blade 24. The slider mechanism 34 also includes a leaf spring 44 having a proximal end secured to the slider mechanism 26 and with a distal end 45 positioned opposing second surface 10b' of the implant 10' within hole 40.

The spring 44 urges the implant 10' towards the handle 22. Slots, aligned with the longitudinal axis of the handle 22 and blade 24, are formed in the handle 22, blade 24 and slider 26 so that the spring 44 may travel to a full rest position shown in FIG. 19. FIG. 13 shows the spring 44 biased against its spring constant to a deflected position.

In the retracted positions of FIGS. 12-14, the spring 44 captures the implant 10' within the hole 40. When the slider mechanism 26 is moved relative to the handle 22, the implant 10' is urged to move with the slider mechanism 26.

FIG. 15-17 illustrate the apparatus 20 in a deployed position with the implant 10' positioned over the hole 25. In the deployed position, the spring 44 urges the implant 10' through the hole 25 to a bottom surface of the handle.

In FIGS. 18-20, the apparatus 20 is shown in the process of being retracted from the surgical site. A bottom side of the distal end of the spring 44 is curved to have a thickness to completely urge the implant through the hole 25. At the bottom surface 24a of the blade 24, the hole 25 is angled outwardly (e.g., at 25a) so that the surfaces of the blade act as a cam surface to ride over the implant 10' to leave the implant in a desired location as will be described.

D. Delivery of Implant

Figure 23:
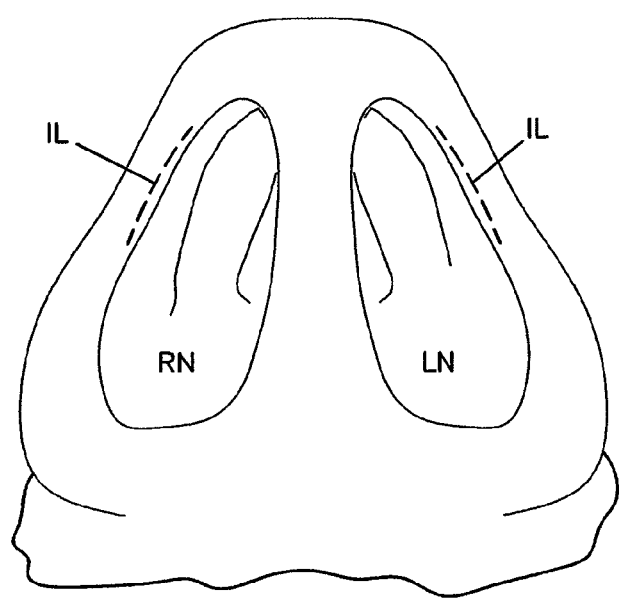
FIG. 23 is a bottom plan view of a nose of a patient showing incision locations for beginning an implantation procedure according to the present invention.

In order to place an implant, the surgeon uses a local anesthetic to anesthetize the incision locations of the nose. FIG. 23 illustrates incision location IL at the alar rim near the nostrils so that the incisions IL do not having a cosmetic appearance for the patient. FIG. 23 shows incision locations IL on both the left and right side of the nose. It will be appreciated that a separate apparatus 20 is used for deploying a separate implant on the left and right sides of the nose.

FIGS. 12-20 illustrate, in sequence, placement of an implant 10' on the left side of the nose with the implant between the cartilages LUC, LLC and an inner mucosal tissue MT. It will be appreciated the implant 10' can be similarly placed between the cartilages LUC, LLC and the outer skin tissue ST.

The surgeon grasps the apparatus 20 which is preloaded with the implant 10' and with the apparatus 20 in the fully retracted position of FIGS. 12-14. The surgeon then makes the incision at the alar rim of the nose using the blade tip 30 to form the incisions.

Using the blade 24 to form a pocket P from the incision location IL to the junction between the upper and lower cartilages, the surgeon advances the tool 20 toward the lower cartilage. The surgeon may guide the tool 20 so that an incision path is formed, at the surgeon's option, against the upper surfaces of the cartilages or against the lower surfaces of the cartilages. Since the tool 20 presents a thickness of extremely low profile, the incision tool 20 forms an incision pathway separating the mucosal layer MT from the cartilages LUC, LLC.

The surgeon advances the tool so that the blade 24 forms a pocket P on the side of the nose (again, at the surgeon's option, between the outer skin tissue ST and the cartilages or between the inner mucosal tissue MT and the cartilages). The pocket P is positioned between the soft tissue layer (mucosal tissue ST in the example of FIG. 13) and opposing the upper and lower cartilages LUC, LLC of the nose. Further, the pocket spans a junction J between the upper and lower cartilages as illustrated in FIG. 13. FIG. 13 illustrates the fully retracted device 20 positioned with the opening 25 spanning the junction J between the upper and lower cartilages LUC, LLC.

When the physician determines that the positioning of FIG. 13 has been achieved, the physician then urges the slider mechanism 26 forward to the position of FIGS. 15-17 at which point the leaf spring 44 urges the implant 10' through the hole 25 and with assurance that the implant 10' is positioned with its length spanning the junction J and with a first surface 10a' of the implant 10' opposing the upper and lower cartilages and with a second surface 10b' of the implant 10' opposing the soft tissue (mucosal tissue MT in FIG. 19).

The surgeon then retracts the apparatus 20 leaving the slide in the deployed position (as shown in FIGS. 18-20). During the retraction, the angled surfaces of the blade 24 permit the blade to ride over the implant 10'. The spring 44 continues to urge against the implant 10' to avoid the implant 10' moving back into the hole 25 and being retracted with the handle.

As illustrated in FIG. 21, when the handle 22 is fully retracted, the implant 10' remains in the pocket P spanning the cartilages LUC, LLC and residing between the cartilages and the mucosal tissue MT. The implant 10', by reason of its material strength, strengthens the cartilages LUC, LLC at the junction and resists excessive inward movement of the cartilages during inhalation.

Particularly on the inside of the nostrils, the mucosal tissue MT is tight against the cartilages LUC, LLC. As a result, sutures or other attachment mechanisms are not necessary since the soft tissue will hold the implant in its desired positioning spanning the junction of the cartilages. However, if desired, the implant could be sutured or, provided with a bio-adhesive for adhering to the cartilages or the soft tissue at the desired positioning. Also, if so desired, the implants can be formed with surfaces to promote tissue in-growth to maintain their relative positioning in the position shown in FIGS. 21 and 22.

Having disclosed the invention in a preferred embodiment, modifications and equivalents may occur to one of ordinary skill in the art. It is intended that such modifications and equivalents be included within the scope of the claims.

What is claimed is:

1. A delivery system for use in a treatment of a nasal valve condition of a patient's nose, said delivery system comprising:
   a. a surgical tool including a blade that is configured to form an access path to create a pocket on a side of said nose with:
      i. said pocket positioned between a soft tissue layer and opposing upper and lower cartilages of said nose, and
      ii. said pocket spanning a junction between said upper and lower cartilages on said side of said nose;
      said surgical tool including an implant tool having an ejector for ejecting an implant from said surgical tool through an opening in the blade, the ejector including a slider mechanism, the slider mechanism including a hole that retains the implant, the slider mechanism configured to transversely align the opening in the blade with the hole solely by being slid along a longitudinal axis of the surgical tool to a forward position, at which a biasing element of the implant tool urges the implant through the hole and the opening solely in a direction transverse to the longitudinal axis of the surgical tool into said pocket, wherein a lower surface of the blade is a cam surface that rides over the implant to maintain the implant in said pocket as the surgical tool is removed;
   b. the implant having a length, width and thickness sized for said implant to reside within said pocket with:
      i. said length sized to span said junction,
      ii. said width sized to be less than a width of said upper and lower cartilages on said side of said nose,
      iii. said thickness separating first and second surfaces of said implant and said thickness sized to be smaller than either of said length and width, and
      iv. said implant further selected to have a stiffness to resist bending in response to inhalation pressures at said nasal valve;
   c. wherein said surgical tool is constructed to carry said implant during formation of the access path.

2. A delivery system according to claim 1 further wherein said implant tool is configured for implanting said implant through said access path and into said pocket with said length oriented for said implant to span said junction, said width oriented for said implant to reside completely on said side of said nose without extending over a bridge of said nose, and said first and second surfaces disposed with said first surface opposing both of said upper and lower cartilages, and with said second surface opposing said soft tissue layer.

3. The delivery system according to claim 1 wherein the biasing element is a leaf spring.

* * * * *